United States Patent [19]
Wohltmann et al.

[11] Patent Number: 5,904,654
[45] Date of Patent: *May 18, 1999

[54] EXCITER-DETECTOR UNIT FOR MEASURING PHYSIOLOGICAL PARAMETERS

[75] Inventors: William J. Wohltmann, San Jose; Mark H. Sher, San Francisco; Bryan F. Flaherty, Half Moon Bay; Richard G. Caro, San Francisco, all of Calif.

[73] Assignee: Vital Insite, Inc., South San Francisco, Calif.

[21] Appl. No.: 08/606,563

[22] Filed: Feb. 26, 1996

Related U.S. Application Data

[60] Provisional application No. 60/005,751, Oct. 20, 1995.

[51] Int. Cl.$^6$ ........................................ A61B 5/02
[52] U.S. Cl. ............................. 600/481; 600/500
[58] Field of Search .................... 128/630, 633, 128/672–696, 748, 660.01, 660.02, 660.03, 653.1; 600/300, 310, 485–509, 561, 437, 438, 439, 407, 481

[56] References Cited

U.S. PATENT DOCUMENTS

| | | |
|---|---|---|
| Re. 32,180 | 6/1986 | Lewiner et al. . |
| 3,090,377 | 5/1963 | Salisbury et al. ...................... 128/2.05 |
| 4,181,134 | 1/1980 | Mason et al. . |
| 4,269,193 | 5/1981 | Eckerle ................................. 128/672 |
| 4,307,728 | 12/1981 | Albert . |
| 4,443,730 | 4/1984 | Kitamura et al. . |
| 4,561,447 | 12/1985 | Kawamura et al. .................... 128/687 |
| 4,646,754 | 3/1987 | Seale ..................................... 128/774 |
| 4,771,792 | 9/1988 | Seale ..................................... 128/774 |
| 4,784,152 | 11/1988 | Shinoda et al. . |
| 4,924,871 | 5/1990 | Honeyager . |
| 5,101,829 | 4/1992 | Fujikawa et al. . |
| 5,394,877 | 3/1995 | Orr et al. .......................... 128/662.03 |

FOREIGN PATENT DOCUMENTS 4-97738  3/1992  Japan .

OTHER PUBLICATIONS

H. Shimazu et al., *Vibration technique for indirect measurement of diastolic arterial pressure in human fingers*, Medical & Biological Engineering & Computing (1989), vol. 27, 130–136.

H. Shimazu et al., *Electric impedance cuff for the indirect measurement of blood pressure and volume elastic modulus in human limb and finger arteries*, Medical and Biological Engineering & Computing (1989), vol. 27, 477–483.

RF and Microwave Designer's Handbook, Watkins–Johnson Co., 1993–1994, pp. 504–510, 766–776.

*Primary Examiner*—Lee Cohen
*Assistant Examiner*—Bryan K. Yarnell
*Attorney, Agent, or Firm*—Flehr Hohbach Test Albritton & Herbert LLP

[57] ABSTRACT

An exciter-detector unit is disclosed which includes an exciter and a detector mounted on a common support for inducing perturbations into the body and detecting the perturbations after they travel a distance through the body in order to detect a hemoparameter.

24 Claims, 4 Drawing Sheets

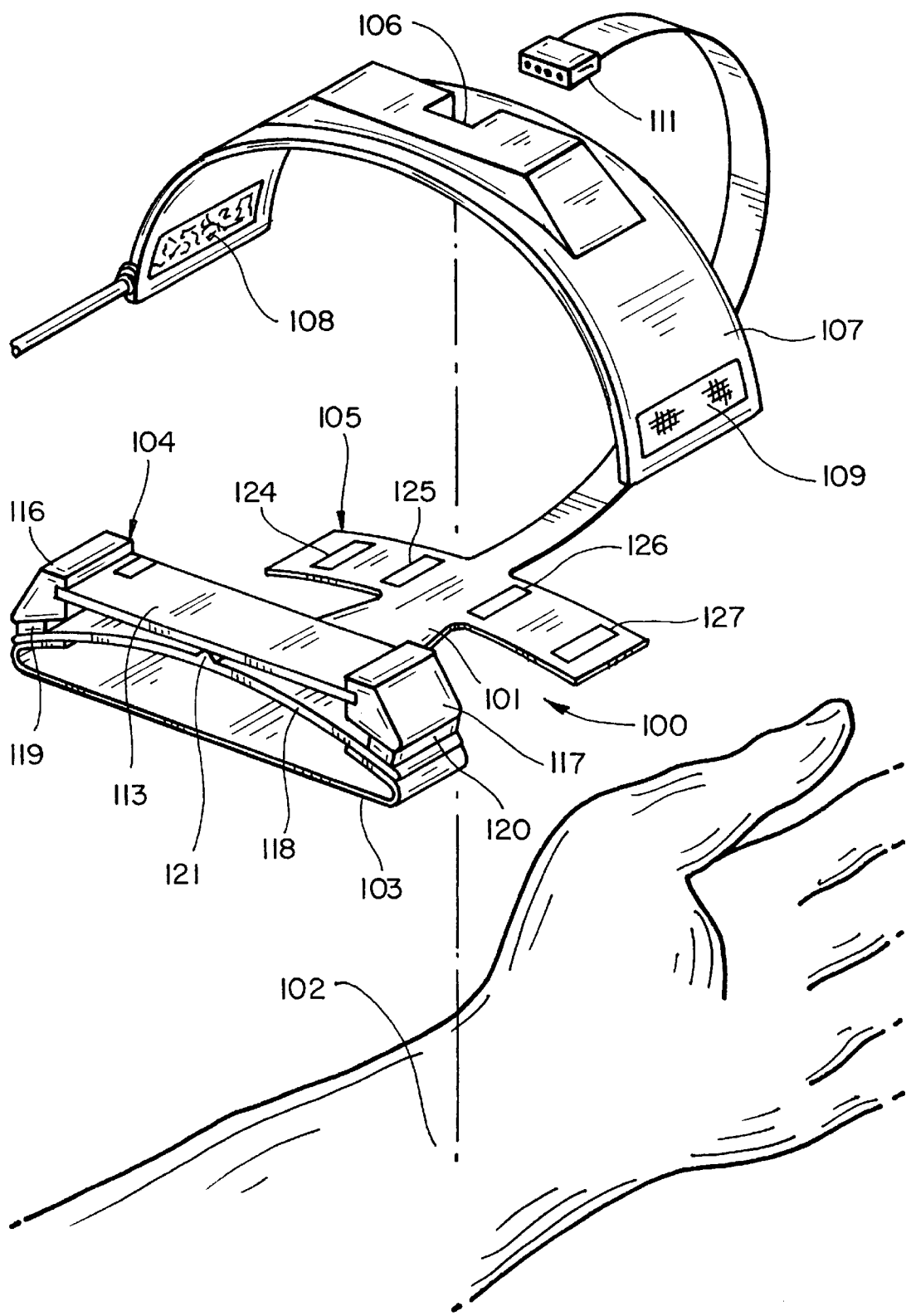
FIG_1

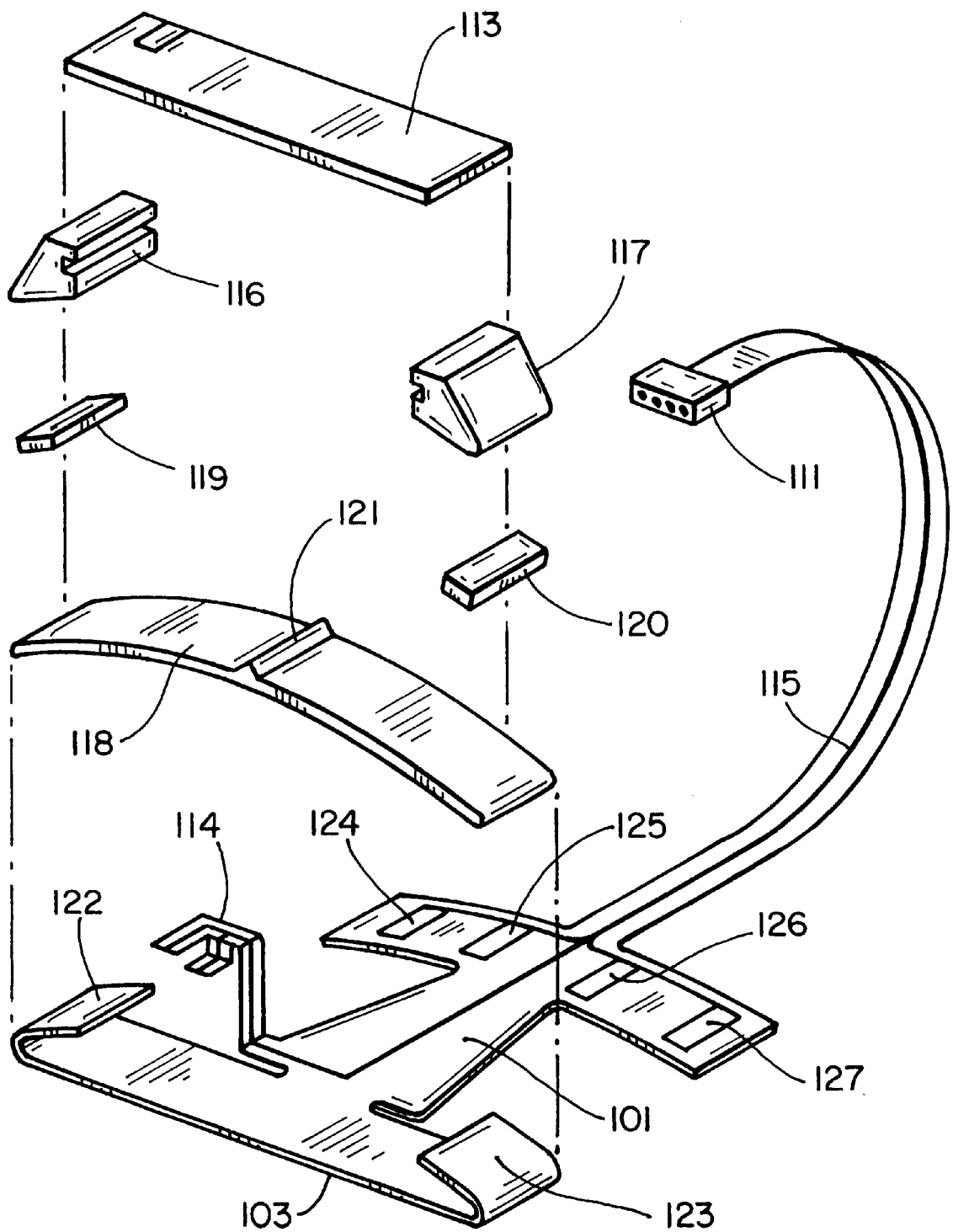
FIG_2

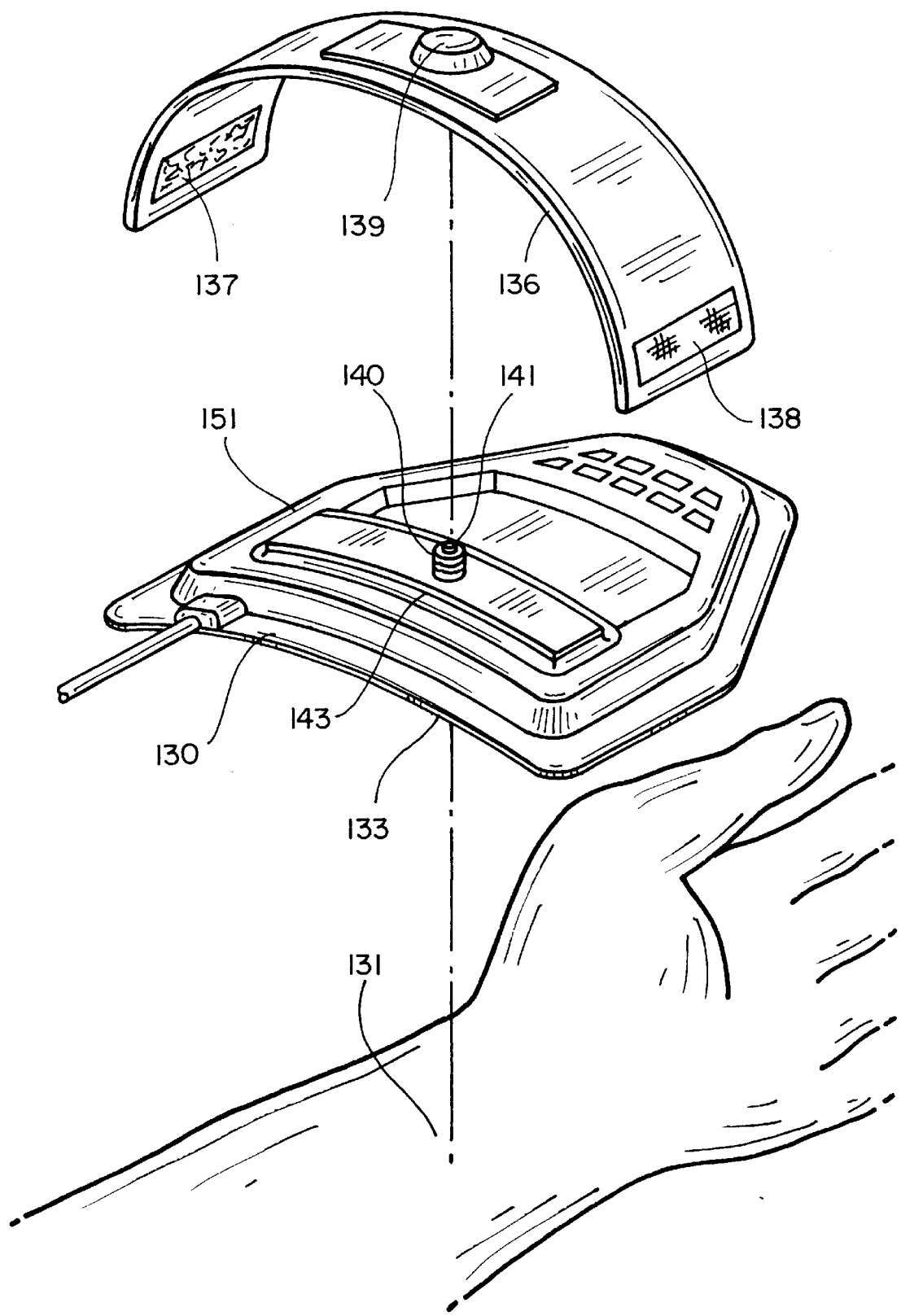
FIG_3

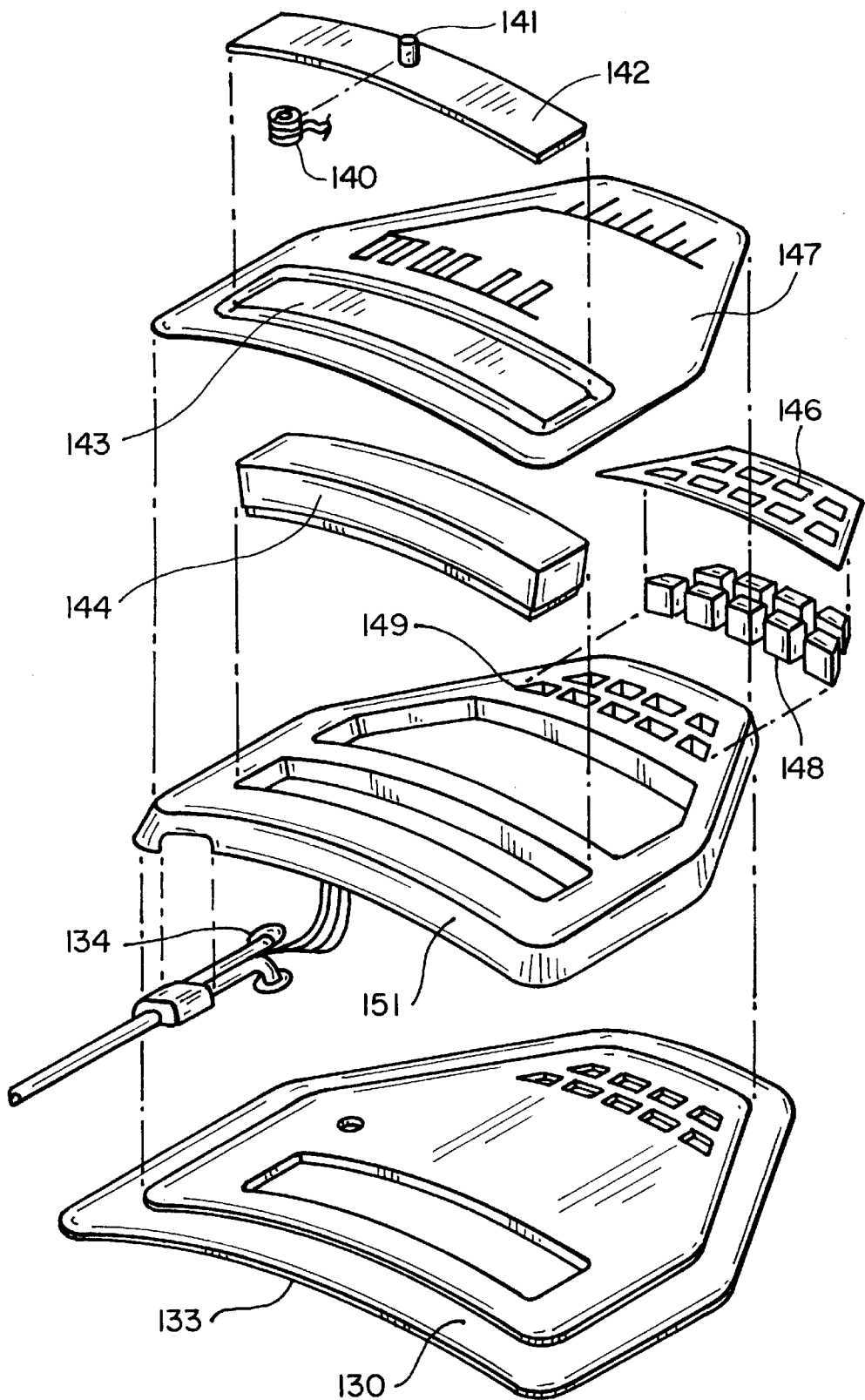
FIG_4

EXCITER-DETECTOR UNIT FOR MEASURING PHYSIOLOGICAL PARAMETERS

RELATED APPLICATION

This application claims the priority of provisional application Ser. No. 60/005,751 filed Oct. 20, 1995 entitled *Exciter-detector Unit for Measuring Physiological Parameters.*

BRIEF SUMMARY OF THE INVENTION

This invention relates generally to an exciter-detector unit and more particularly to an assembly which includes an exciter and a detector mounted on a common support for inducing perturbations into the body and detecting the perturbations after they travel a distance through the body.

BACKGROUND OF THE INVENTION

In copending applications Ser. No. 08/228,213, now U.S. Pat. No. 5,590,649, and continuation-in-part applications Ser. Nos. 08/561,923 and 08/556,547, both applications pending, (Flehr Hohbach Test Albritton & Herbert files A-59155-1 and A-59155-2, respectively), and Flehr Hohbach Test Albritton & Herbert file No. 08/561 928, which was submitted to the U.S. Patent Office for filing on Nov. 22, 1995, there is described an apparatus for measuring a perturbation induced in the body to determine physiological parameters. The apparatus disclosed in said applications includes an exciter positioned over a blood vessel of the patient for inducing a transmitted exciter waveform into the patient. A non-invasive sensor is spaced from the exciter over the blood vessel. The non-invasive sensor is configured to sense a hemo-parameter and to generate a non-invasive sensor signal representative of the hemo-parameter containing a component of a physiological parameter waveform and a component of a received exciter waveform. In this context, a hemo-parameter is defined as any physiological parameter related to vessel blood such as pressure, flow, volume, velocity, blood vessel wall motion, blood vessel wall position and other related parameters. A processor determines the relationship between a property of the received exciter waveform and a property of the physiological parameter to provide the physiological parameter. In one embodiment, the physiological parameter measured is blood pressure. Exciters, sensors and processors can also be used to analyze and track other physiological parameters such as vascular wall compliance, strength of ventricular contractions, vascular resistance, fluid volume, cardiac output, myocardial contractility and other related parameters. It will be apparent that use of the present exciter-detector unit is not limited to use in the foregoing apparatus.

OBJECTS AND SUMMARY OF THE INVENTION

The exciter-detector unit can take the form of several embodiments. However, common to all embodiments is the combination of an exciter and a detector in a single-unit assembly for convenient attachment to the body.

It is an object of this invention to provide a single-unit exciter-detector assembly wherein the separation between the exciter and detector remains substantially constant after attachment to the patient.

It is another object of the invention to provide a single-unit exciter-detector assembly which conforms to the body of the patient to make good contact with a variety of body-shape parts and different patients.

It is another object to provide a single-unit exciter-detector assembly which can be firmly attached to the body to prevent movement during monitoring.

The foregoing and other objects are achieved by an exciter-detector assembly which includes a support member adapted to be placed on the body and which supports an exciter for transmitting perturbations into the body at a first location and a detector spaced from the exciter for detecting the perturbations to provide an output signal response to the perturbations.

BRIEF DESCRIPTION OF THE DRAWINGS

The foregoing and other object of the invention will be more fully understood from the following description read in connection with the accompanying drawings, of which:

FIG. 1 is a partially exploded view of an exciter-detector unit in accordance with one embodiment of the invention.

FIG. 2 is an exploded view of the unit of FIG. 1;

FIG. 3 is a partially exploded view of another exciter-detector unit in accordance with another embodiment of the invention; and FIG. 4 is an exploded view of the unit shown in FIG. 3.

DESCRIPTION OF THE PREFERRED EMBODIMENTS

Referring to FIG. 1, the unit includes an assembly 100 which includes a support member 101 placed on the patient's wrist 102 with a suitable adhesive 103 on the underside of the member 101. The assembly includes an exciter 104 and a detector 105 mounted on the support member 101. The assembly 100 may be further held in place by a cover 107 which includes a recess 106 for the exciter 104. The cover 107 is wrapped around the patient's wrist and held in place by Velcro hooks 108 and Velcro latches 109. Electrical connections (not shown) are made to the detector and sensor by thin conductive film leads formed in the support member 101. The leads terminate in a connector 111. Thus, the exciter and detector are maintained in spaced relationship in contact with the patient by the support member 101.

Referring particularly to FIGS. 1 and 2, a suitable exciter assembly includes a piezoelectric member 113 which contains upper and lower conductive films which make electrical connection to connectors 114 and to the connector 111 via the thin film leads 115. Spaced plastic clamps 116, 117 hold the ends of the piezoelectric member 113. The piezoelectric member is an element made of PZT (lead zirconium titanate) which has a bending axis offset from that of a thin metallic foil on which it is mounted. For this reason, application to the assembly of an alternating voltage while fixing its ends with clamps 116, 117, causes the center of the element to vibrate along the axis normal to the assembly and towards the tissue.

A plastic plunger 118 transfers vibrations from the piezoelectric member 113 to the flexible support member 101 which is in intimate contact with the body portion. Low density foam positioners 119, 120 are glued to clamps 116, 117 and plunger 118, clamps 116, 117 and piezoelectric member 113 in place on the support member 101. The plastic plunger 118 transfers the vibrations from the piezoelectric member 113 via the plunger ridge 121 to the support member or base 101. The base has two flaps 122, 123 suitably attached to the plunger 118 as by adhesive or heat bonding. The base or support member 101 includes a detector comprising four spaced electrodes 124, 125, 126, 127 which are in contact with the patient and form an impedance plethysmogram. The outermost electrodes 126, 127 are connected to a source of constant alternating current with an oscillation frequency in the range of 20 kHz and a substantially constant amplitude. A voltage measurement device is connected across the inner pair of electrodes 125, 126. The voltage measured across this pair of electrodes is proportional to the impedance of the tissue between and below these electrodes. This impedance is in turn a measure of the composition of that tissue. Thus, in the case in which an artery under the sensor between the electrodes 125, 126 alternately expands and contracts, thus varying the amount of highly conductive blood in the current path, a signal is generated representative of the arterial volume.

FIG. 3 shows the second preferred embodiment wherein a piezoelectric detector is used, coupled to the tissue by means of conformal gels. Furthermore, this detector is fabricated so as to incorporate an array of detector elements. This embodiment allows the device to be relatively position-insensitive, since only one of the detector elements need be in the appropriate position for vibration sensing in the tissue of choice. Signals from that detector can then be chosen by software for analysis, while those from the other elements are discarded.

A two-part electromagnetic voice coil assembly is used as the exciter assembly, with a gel bag acting as a conformal connection to the body. The entire single-unit assembly is held to the body with a vacuum.

The exciter-detector assembly includes a base 130 held on a patient's arm 131 by an adhesive film 133, and held in place by a vacuum between the base 130 and arm 131 applied through conduit 134. A cover 136 may wrap around the patient's wrist and be held in place by Velcro 137, 138. The cover is placed over the assembly so that the magnet 139 is aligned with the armature 140 and plunger 141 of the exciter. The plunger 141 is bonded to a plastic member 142 which is attached to a flexible membrane 143 in contact with a gel member 144 which transfers vibrations from the electromagnetic exciter plunger 141 to the patient. The detector includes a plurality of transducers 146 bonded to top 147. The transducers are driven by detector gels 148 retained in the keyways 149 formed in the base member 151. The gels transfer motion between the patient and the transducers.

Two exciter and detector single-unit assemblies have been described. It is apparent that the exciter can use a diverse selection of technologies, each of which may pertain to a separate embodiment, and each of which has the common feature of being able to generate a controlled vibration which can be coupled to the body in a localized and controlled way. Examples of appropriate technologies include, but are not limited to pneumatic bladder, piezoelectric, electromagnetic (buzzer, solenoid, etc.), voice coil system, magnetostrictive, electrostatic, and mechanical vibration. The following are descriptions of specific exciter technologies.

Pneumatic Bladder: This exciter technology involves the pressurization of a conformal bladder with a source of fluid pressure which can be modulated at the frequency of desired vibration. An example is a voice coil or loud speaker used to vibrate a column of air connected to a conformal plastic "bubble" placed in contact with the tissue.

Piezoelectric: This exciter technology involves the use of a piezoelectric element mounted on a flexible structure, such as plastic film, in such a way that the bending axis of the structure is offset from the center of the piezoelectric element. The structure is held at the edges in a mount. When a voltage is applied to the piezoelectric element, it either stretches or contracts, according to the polarity of the applied voltage, resulting in bending of the structure in one of two dimensions. This bending can be used to apply a force to a segment of the body. By alternating the voltage polarity, a vibration can be coupled to the body.

Electromagnetic (buzzer, solenoid, etc.): This exciter technology involves the use of an electromagnetic technology such as a buzzer to produce a vibrating element which can be transmitted to the body by a variety of load-distributing elements.

Voice Coil System: This exciter technology involves the use of a current-carrying coil, positioned within a magnet. The use of alternating current causes oscillation of the coil within the magnet as can be seen in a loudspeaker. In this application, the coil can be connected to a load-distributing element and a vibration can be coupled to the body. In an additional refinement, the assembly can be split into two parts wherein the coil is attached to the single-unit assembly of this invention, while the magnet is held within the mounting assembly used to cover the single-unit assembly on the body.

Magnetostrictive: This exciter technology involves the use of the phenomenon of magnetostriction to cause a vibration which can be coupled to the body.

Electrostatic: This exciter technology involves the use of attraction or repulsion which can be set between two plates with opposite or similar charge. By alternating the polarity of charge on one plate, the plates alternately attract and repel each other, causing an element attached to one plate to vibrate compared to the other.

Mechanical Vibration (e.g. electric massager): This exciter technology involves the use of a mechanically vibrating element such as can be seen in an electric massager. Vibration derives from an oscillating or rotating shaft from a motor and may involve the use of a cam or other device to convert a uniform rotation to a longitudinal or transverse vibration.

The detector can use a diverse selection of technologies, each of which may pertain to a separate embodiment, and each of which has the common feature of being able to detect a vibration which has propagated through a portion of the body. Examples of appropriate technologies include, but are not limited to piezoelectric, photo-plethysmography, impedance plethysmography, other plethysmography, capacitive displacement, inductive displacement, doppler ultrasound/light, ultrasound and other wall displacement, microwave impedance, strain gage, tonometry and electronic flow meter. The following are descriptions of specific detector technologies.

Piezoelectric: This detector technology involves a piezoelectric element positioned in a geometry so that it is stressed by movement of the underlying tissue. An example is in the case of placement of a thin piezoelectric film over the radial pulse at the wrist. Following arterial pulsation, the skin and tissue move and the piezoelectric element is bent. If mounted so as to have a bending axis not at the geometrical axis of the film, this will set up a stress in the piezoelectric material and lead to the generation of a measurable charge and voltage.

Photo-plethysmography: This detector technology involves the use of a light transmitted through partially absorbing tissue and being detected at the other side (or after reflection within the tissue). In the case in which vibration of the tissue, or of a component of the tissue, causes a change in the magnitude of absorption per length, the light propagation path length or both, a change in light intensity at the detector will be measured; thus, a signal related to the vibration will be detected. An example of this is the use of photo-plethysmography for detection of arterial pulsation in pulse oximetry.

Impedance Plethysmography (including microwave): This detector technology involves the use of a similar concept to that of photo-plethysmography, except that an electrical current is passed through the region of tissue of interest and the electrical impedance across the tissue is measured. The impedance is sensitive to a change in tissue volume, density or composition, and is also commonly used to detect arterial pulsations. This could also be performed in the microwave region of the spectrum using the tissue impedance of a microwave antenna to monitor tissue motion or density or composition changes.

Other Plethysmography (including strain gage): This detector technology involves the use of other techniques for measuring the volume change in a segment of tissue and can include the techniques of strain gage plethysmography and of mercury resistance plethysmography, all know to those skilled in the art.

Capacitive Displacement: This detector technology involves the use of a detector configured so that one plate of a capacitor is made to be in effective contact, and therefore moved by vibrations in, a plane of tissue; the other plane is fixed. Thus, vibration of the tissue plane causes relative motion of the two plates and a change of the capacitance of the structure.

Inductive Displacement: This detector technology involves the use of a similar detector in which the electrical element used to connect to the tissue plane is an inductor wherein the inductance is responsive to the position of the tissue plane in relation to a fixed element of the detector.

Doppler Ultrasound/light: This detector technology involves the use of ultrasound or light, scattered from moving tissue. The scattered radiation undergoes a Doppler shift of magnitude related to the speed of motion of the scattering tissue plane. Thus, for example, upon reversal of the motion of the tissue at extremes of vibration, the sign of the Doppler frequency shift is reversed. Thus, frequency shift can be used to monitor a vibratory motion.

Ultrasound and other Wall Displacement: This detector technology involves the use of ultrasound and other radiation which can be scattered from a moving tissue plane such as an artery wall. The time of flight of the radiation from scattering to detection is measured and converted to a signal representative of the position of the scattering site. In this way, motion of a tissue plane can be monitored.

Tonometry: This detector technology involves the use of a force sensor to directly measure the force applied to it by a vibrating tissue sample.

Electronic Flow Meter: This detector technology involves the use of an electromagnetic flow meter responsive to the flow of charged material, such as blood, to monitor changes in flow through an arterial vessel and the associated pressure changes.

It will be clear to those skilled in the art that a functional single-unit assembly can be made using any pair of technologies listed above as detector or exciter technologies in the single-unit exciter-detector assembly of this invention. The assembly may be held in intimate contact with the body by adhesive, adhesive tape, vacuum or pressure, or the like. The interface may include gel, fluid, rubber or foam.

Thus, there has been described a single-unit exciter-detector assembly which is attached to the patient in such a way that the overall pressure over the assembly can be varied in a controlled way in order to modify the pressure experienced by the underlying tissue. An example would be in the case of use of the single-unit assembly for measurement of blood pressure in which the ability to modulate the transmural arterial pressure facilitates determination of the relationship between the velocity of propagation of the excitation along the artery and blood pressure, the physiological parameter under investigation.

What is claimed:

1. An exciter-detector unit for measuring physiological parameters of a patient comprising:
   a support member adapted to be placed on the patient, an exciter mounted on said support member for transmitting perturbations into the patient at a first location, and
   a detector mounted on said support member spaced a predetermined distance along the support member from said exciter for detecting a hemoparameter and to provide an output signal containing a component of a physiological parameter waveform and a component of received perturbations.

2. An exciter-detector assembly as in claim 1 wherein the support member is rigid with a conformal layer for contacting the body.

3. An exciter-detector assembly as in claim 1 wherein the support member is made of conformal material.

4. An exciter-detector assembly as in claim 1 which includes means for firmly attaching said assembly to the body to prevent movement during monitoring.

5. An exciter-detector assembly as in claim 1 wherein the exciter includes a piezoelectric element.

6. An exciter-detector assembly as in claim 1 wherein the exciter includes an electromagnetic element.

7. An exciter-detector assembly as in claims 1, 5 or 6 wherein the detector includes a piezoelectric element.

8. An exciter-detector assembly as in claims 1, 5 or 6 wherein the detector includes a plurality of piezoelectric elements.

9. An exciter-detector assembly as in claim 1 wherein the exciter includes a magnetostrictive element.

10. An exciter-detector assembly as in claim 1 wherein the exciter includes an electrostatic element.

11. An exciter-detector assembly as in claim 1 wherein the detector is a plethysmography detector.

12. An exciter-detector assembly as in claim 1 wherein the detector is a displacement detector for detecting movement of underlying tissue.

13. An exciter-detector assembly as in claim 1 wherein the detector is responsive to force exerted by the body.

14. An exciter-detector unit for measuring physiological parameters at selected positions on the body of a patient comprising:
   an exciter for transmitting vibrations into the patient at a first location at said position, and
   a detector spaced from said exciter for detecting a hemoparameter at a second location to provide an output signal containing a component of a physiological parameter waveform and a component of received vibrations, and
   an elongated support member for supporting said exciter and detector at a predetermined fixed spacing along said elongated support member.

15. An exciter-detector assembly as in claim 14 wherein the support member is rigid with a conformal layer for contacting the body.

16. An exciter-detector assembly as in claim 15 wherein the exciter includes a conformal gel for contacting the body to transmit perturbations to the body.

17. An exciter-detector assembly as in claim 15 wherein the detector includes a conformal gel for contacting the body to receive the vibrations and applying them to a transducer.

18. An exciter-detector assembly as in claim 17 wherein the exciter includes a conformal gel for contacting the body to transmit perturbations from a transducer to the body.

19. An exciter-detector assembly as in claim 15 including a plurality of detectors, each of which includes a conformal gel for contacting the body to receive perturbations and applying them to a transducer.

20. An exciter-detector assembly as in claim 14 wherein the support member is made of conformal material.

21. An exciter-detector assembly as in claim 20 wherein the support member is adapted to be attached to the body with an adhesive.

22. An exciter-detector assembly as in claim 21 including a cover member adapted to be wrapped around the wrist to hold the exciter-detector unit.

23. An exciter-detector assembly as in claim 14 which includes means for firmly attaching said assembly to the body to prevent movement during monitoring.

24. An exciter-detector assembly as in claim 14 wherein the detector is responsive to force exerted by the body.

* * * * *